United States Patent
Lv et al.

(10) Patent No.: US 9,765,098 B2
(45) Date of Patent: Sep. 19, 2017

(54) PREPARATION METHOD OF 3,7,11-TRIMETHYLDODEC-2,4,6,10-TETRAENE-1-YL-PHOSPHONIC SALT

(71) Applicants: NANJING UNIVERSITY OF TECHNOLOGY, Nanjing (CN); Zhejiang Medicine Co., Ltd. Xinchang Pharmaceutical Factory, Donglu (CN)

(72) Inventors: Chunlei Lv, Huancheng Donglu (CN); Shiqing Pi, Huancheng Donglu (CN); Jianhui Chen, Huancheng Donglu (CN); Dingqiang Lu, Huancheng Donglu (CN); Pingkai Ouyang, Huancheng Donglu (CN)

(73) Assignees: Nanjing University of Technology, Nanjing (CN); Zhejiang Medicine Co., Ltd., Donglu (CN)

( * ) Notice: Subject to any disclaimer, the term of this patent is extended or adjusted under 35 U.S.C. 154(b) by 0 days.

(21) Appl. No.: 14/369,102

(22) PCT Filed: Dec. 10, 2012

(86) PCT No.: PCT/CN2012/001668
§ 371 (c)(1),
(2) Date: Jun. 26, 2014

(87) PCT Pub. No.: WO2013/097286
PCT Pub. Date: Jul. 4, 2013

(65) Prior Publication Data
US 2014/0378709 A1 Dec. 25, 2014

(30) Foreign Application Priority Data
Dec. 26, 2011 (CN) .......................... 2011 1 0440231

(51) Int. Cl.
C07F 9/54 (2006.01)
C07F 9/00 (2006.01)

(52) U.S. Cl.
CPC .......... *C07F 9/5442* (2013.01); *C07F 9/5428* (2013.01)

(58) Field of Classification Search
CPC ........................... C07F 9/5442; C07F 9/5428
USPC ............................................................ 568/9
See application file for complete search history.

(56) References Cited

U.S. PATENT DOCUMENTS 6,423,873 B1 * 7/2002 Wegner et al. .................. 568/9
2007/0123726 A1 * 5/2007 Szarvas et al. ............... 554/222

OTHER PUBLICATIONS

Suga et al., Grignard reaction of vinyl chloride with alph-beta-unsaturated carbonyl compounds (Yuki Gosei Kagaku Kyokaishi (1966), 24 (3), 213-215.*

* cited by examiner

*Primary Examiner* — Jafar Parsa
(74) *Attorney, Agent, or Firm* — Christopher Casieri; William Hare

(57) ABSTRACT

Provided in the present invention is a preparation method for a phosphonic salt, comprising the step of: reacting 3,7,11-trimethyldodec-1,4,6,10-tetraene-3-ol with triarylphosphine and an acid in an alcohol solvent at 50-100° C. to form the phosphonic salt, wherein the acid is a sulfamic acid or methanesulfonic acid, and the alcohol solvent is a straight chain monohydric alcohol containing 1-5 carbon atoms. The method is performed in nearly neutral conditions, greatly reducing the generation of impurities and greatly obtaining phosphonic salt with an increased E content. The yield of lycopene obtained by using the phosphonic salt as a raw material is high.

14 Claims, No Drawings

PREPARATION METHOD OF 3,7,11-TRIMETHYLDODEC-2,4,6,10-TETRAENE-1-YL-PHOSPHONIC SALT

CROSS-REFERENCE TO RELATED APPLICATIONS

This application is a national phase application of PCT/CN2012/001668, filed on Dec. 10, 2012, which claims priority to Chinese Application No. 201110440231.0 filed on Dec. 26, 2011.

FIELD OF THE INVENTION

The present invention relates to a preparation method of 3,7,11-trimethyldodec-2,4,6,10-tetraene-1-yl phosphonic salt.

BACKGROUND OF THE INVENTION

EP0382067 and U.S. Pat. No. 5,166,445 describe a preparation method of C15 phosphonic salt by reacting 3,7,11-trimethyldodec-1,4,6,10-tetraene-3-ol with a triarylphosphine and a lower alkanoic acid. During the process, the phosphonic salt of alkanoic acid must be converted into halogenide by anion exchange prior to final Witting reaction. (Z)-phosphonic salt isomers are removed by crystallization process in order to achieve higher E/Z ratio of lycopene, wherein, Z refers to cis-isomer and E refers to trans-isomer, and the following is the same.

EP0895997, U.S. Pat. Nos. 6,187,959, 6,433,226, 6,423,873, 6,603,045 and CN1319600 describe a preparation method of C15 phosphonic salt by reacting 3,7,11-trimethyldodec-1,4,6,10-tetraene-3-ol with a triarylphosphine and strong acids such as sulfonic acid, sulfuric acid, etc., and using a solvent of lower alkanoic acid, wherein a E/Z ratio of the obtained phosphonic salt is between 4~5:1. A yield of the obtained phosphonic salt is higher than that of C15 phosphonic salt in EP0382067 and U.S. Pat. No. 5,166,445 and the E/Z ratio of obtained phosphonic salt is higher than that of C15 phosphonic salt in EP0382067 and U.S. Pat. No. 5,166,445.

All of the prior patents' methods require use of lots of lower alkanoic acids such as formic acid, acetic acid, or propionic acid as reactant or solvent. But there are two deficiencies: (1) heating and stronger acid are simultaneously in the process, it makes polyene-bonds phosphonic salt contain amounts of undesired impurities and obtain phosphonic salt with deeper color; (2) plenty of organic acid will bring greater process cost, equipment corrosion and environmental pollution.

SUMMARY OF THE INVENTION

The purpose of the present invention is to provide an improved preparation method of C15 phosphonic salt, wherein undesired impurities of 3,7,11-trimethyldodec-2,4,6,10-tetraene-1-yl phosphonic salt are greatly reduced, and the E content of isomers is very high after purification and at the same time plenty of organic acid is removed.

According to the preparation method of 3,7,11-trimethyldodec-2,4,6,10-tetraene-1-yl phosphonic salt of Formula I of the present invention, the method comprises reacting 3,7,11-trimethyldodec-1,4,6,10-tetraene-3-ol of Formula II with triarylphosphine and an acid in an alcohol solvent and at a temperature of 50~100° C., to produce a phosphonic salt of Formula I,

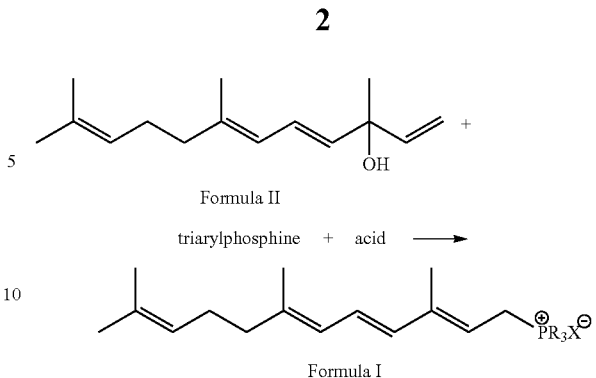

Wherein the acid is sulfamic acid or methanesulphonic acid, the alcohol solvent is a straight-chain monohydric alcohol containing C1~C5, preferably, methanol or ethanol; the reaction temperature is 60~65° C.; R is phenyl; X is an anion of sulfamic acid or methanesulphonic acid.

The tertiary alcohol of Formula II can be obtained by reacting pseudoionone with a chloroethylene Grignard reagent. The acid is dropped into the reaction system containing the tertiary alcohol of Formula II, triphenylphosphine and an alcohol solvent, in order to ensure the reaction system maintaining a weak acidity or neutralization. An E/Z ratio of the phosphonic salt of Formula I is 2.5:1.

Wherein 100 ml deionized water is added into the phosphonic salt of Formula I, and then extracted with 500 ml n-hexane for 3~5 times, the n-hexane recycled for reutilization, and then extracted with a methanol solution containing the phosphonic salt of Formula I with 2000 ml of dichloromethane to obtain a dichloromethane solution containing phosphonic salt of Formula I, and then obtain the phosphonic salt of Formula I after removing the solvent.

Wherein the dichloromethane solution containing phosphonic salt of Formula I is washed with 500 ml of 5% sodium bromide aqueous solution each time for 3 times, and then adding 1500 ml ethyl acetate into a dichloromethane layer after removing dichloromethane, and evaporate 500 ml of a mixed solution containing dichloromethane and ethyl acetate, and then cool the residue to produce crystals, and then filtrate and dry, to produce a phosphonic salt of Formula I with E/Z ratio of 1:11.5 and a phosphonic salt of Formula I with E/Z ratio of 94.5:1 after removing solvent of a mother liquor.

The method of the present invention can convert vinyl pseudoionol of Formula II into a corresponding phosphonic salt, the yield is larger than 95%, and the selectivity of E/Z is larger than 2.5:1. Phosphonic salt with an E/Z ratio larger than 7:1 are obtained after crystallizing and purifying. Z is the cis-isomer, and E is the trans-isomer.

Advantages of the method of the present invention are to replace the organic acid with an alcohol solvent and to perform in nearly neutral conditions, greatly reduce generation of impurities and greatly obtain phosphonic salt with an increased E content. The yield of lycopene obtained by using the phosphonic salt as a raw material is high.

DETAILED DESCRIPTION OF THE PRESENT INVENTION AND PREFERRED EMBODIMENTS THEREOF

Hereafter, the present invention will be described specifically with reference to the examples. The examples are given only for illustration of the technical solution of the present invention and should not be construed to limit the present invention.

EXAMPLE 1

(1) Triphenylphosphine (288 g, 1.1 mol), vinylpseudoionol (252 g, 96%, 1.14 mol) and 1000 ml methanol are mixed, and a solution of methanesulfonic acid (96 g, 1.0 mol) dissolved in 200 ml methanol at temperature of 60~65° C. added to it, allowed to react for 2 hr under heat preservation after finishing the addition, and the pH of the solution is neutral.

The reaction mixture appears faint yellow. The reaction mixture is analyzed by HPLC to find that vinylpseudoionol is completely converted to phosphonic salt and its E/Z ratio is 2.5:1. Then 100 ml of deionized water is added into the reaction mixture, extracted with 500 ml of n-hexane for 3~5 times, and recycle n-hexane layer for reutilization, and the extracted unreacted triphenylphosphine may be crystallized for reutilization. The methanol in methanol solution containing phosphonic salt is recycled, and the solution is extracted by 2000 ml dichloromethane to obtain 626 g of phosphonic salt after removing the solvent, the yield of the phosphonic salt is 98%, and the content of the phosphonic salt analyzed by HPLC is 95%.

(2) Refinement: a dichloromethane solution of the phosphonic salt obtained from the step (1) is washed with 500 ml of 5% sodium bromide aqueous solution each time for 3 times to obtain a dichloromethane layer after recycling most of dichloromethane, and 1500 ml of ethyl acetate is added, and then 500 ml of a mixed solution containing dichloromethane and ethyl acetate is evaporated, and a residue is cooled and crystallized, and then obtain 195 g of phosphonic salt after filtrating and drying, its E/Z ratio is 1:11.5, and then obtain 423 g of solid after removing solvent in mother liquor, its E/Z ratio is 94.5:1, and the yield of refinement is 67.6%, and the total yield of two steps (1) and (2) is 66.1%.
Determination of Product Structure:

$^1$HNMR (δ, ppm,400 MHz, MeOD): 1.45, 1.55, 1.65, 1.76(s, 12H, $CH_3$); 2.05~2.07, 2.15~2.18(m, 4H, $CH_2$); 4.66~4.72(m, 2H, P—$CH_2$); 5.06~5.08, 5.30~5.33, 5.80~5.82, 6.00~6.03, 6.32~6.36 (m, 5H, C=CH, CH=CH); 7.72~7.88(m, 15H, ph).

$^{13}$CNMR (δ, ppm, 100 MHz, MeOD): 13.2; 17.5; 24.1; 25.6; 32.6; 40.4; 117.0; 137.6; 125.5; 127.6; 130.4; 132.6; 133.8; 135.0; 141.1; 143.6; 146.8.

EXAMPLE 2

(1) Triphenylphosphine (288 g, 1.1 mol), vinylpseudoionol (220.1 g, 96%, 1.0 mol) and 1000 ml absolute ethanol are mixed, and a solution of sulfamic acid (96 g, 1.0 mol) dissolved in 200 ml absolute ethanol at temperature of 50~55° C. is added to it, to react for 2 hr under heat preservation after finishing the addition, and the pH of the solution is neutral. The reaction mixture appears faint yellow. The reaction mixture is analyzed by HPLC to find that vinylpseudoionol is completely converted to phosphonic salt and its E/Z ratio is 2.4:1. Next 100 ml of deionized water is added into the reaction mixture, extracted with 500 ml of n-hexane for 3~5 times, and a ethanol solution containing phosphonic salt is recycled, and the solution is extracted by 2000 ml dichloromethane to obtain 539 g phosphonic salt after removing solvent, the yield of the phosphonic salt is 96%, and the content of the phosphonic salt analyzed by HPLC is 97%.

(2) Refinement: a dichloromethane solution of the phosphonic salt obtained from the step (1) is washed with 500 ml of 5% sodium bromide aqueous solution each time for 3 times to obtain a dichloromethane layer after recycling most of dichloromethane, and 1500 ml of ethyl acetate is added, and then 500 ml of a mixed solution containing dichloromethane and ethyl acetate is evaporated, and a residue is cooled and crystallized, and then obtain 165 g of phosphonic salt after filtrating and drying, its E/Z ratio is 1:11.5, and then obtain 362 g of solid after removing solvent in mother liquor, its E/Z ratio is 94.5:1, and the yield of refinement is 64.4%, and the total yield of two steps (1) and (2) is 61.8%.
Determination of Product Structure:

$^1$HNMR (δ, ppm,400 MHz, MeOD): 1.45, 1.55, 1.65, 1.76(s, 12H, $CH_3$); 2.05~2.07, 2.15~2.18(m, 4H, $CH_2$); 4.66~4.72(m, 2H, P—$CH_2$); 5.06~5.08, 5.30~5.33, 5.80~5.82, 6.00~6.03, 6.32~6.36 (m, 5H, C=CH, CH=CH); 7.72~7.88(m, 15H, ph).

$^{13}$CNMR (δ, ppm, 100 MHz, MeOD): 13.2; 17.5; 24.1; 25.6; 32.6; 40.4; 117.0; 137.6; 125.5; 127.6; 130.4; 132.6; 133.8; 135.0; 141.1; 143.6; 146.8.

EXAMPLE 3

(1) Triphenylphosphine (288 g, 1.1 mol), vinylpseudoionol (220 g, 96%, 1.0 mol) and 1000 ml propanol are mixed, and a solution of methanesulfonic acid (96 g, 1.0 mol) dissolved in 200 ml propanol at temperature of 90~98° C. is added to it, to react for 2 hr under heat preservation after finishing the addition, and the pH of the solution is neutral. The reaction mixture appears faint yellow. The reaction mixture is analyzed by HPLC to find that vinylpseudoionol is completely converted to phosphonic salt and its E/Z ratio is 2.0:1. 200 mL of deionized water is added into the reaction mixture, extracted with 500 ml n-hexane for 3~5 times, and then the n-hexane layer is recycled for reutilization, and the extracted unreacted triphenylphosphine may be crystallized for reutilization. The propanol in propanol solution containing phosphonic salt is recycled, and the solution is extracted by 2000 ml dichloromethane to obtain 535 g phosphonic salt after removing solvent, the yield of the phosphonic salt is 95.3%, and the content of the phosphonic salt analyzed by HPLC is 95%.

(2) Refinement: a dichloromethane solution of the phosphonic salt obtained from the step (1) is washed with 500 ml of 10% sodium bromide aqueous solution each time for 2 times to obtain a dichloromethane layer after recycling most of dichloromethane, and 1500 ml of ethyl acetate is added, and then 500 ml of a mixed solution containing dichloromethane and ethyl acetate is evaporated, and a residue is cooled and crystallized, and then obtain 134 g of phosphonic salt after filtrating and drying, its E/Z ratio is 0.5:11.5, and obtain 407 g of solid after removing solvent in mother liquor, its E/Z ratio is 95.5:0.5, and the yield of refinement is 76.1%, and the total yield of two steps (1) & (2) is 72.5%.
Determination of Product Structure:

$^1$HNMR (δ, ppm,400 MHz, MeOD): 1.45, 1.55, 1.65, 1.76(s, 12H, $CH_3$); 2.05~2.07,2.15~2.18(m, 4H, $CH_2$); 4.66~4.72(m, 2H, P—$CH_2$); 5.06~5.08, 5.30~5.33, 5.80~5.82, 6.00~6.03, 6.32~6.36 (m, 5H, C=CH, CH=CH); 7.72~7.88(m, 15H, ph).

$^{13}$CNMR (δ, ppm, 100 MHz, MeOD): 13.2; 17.5; 24.1; 25.6; 32.6; 40.4; 117.0; 137.6; 125.5; 127.6; 130.4; 132.6; 133.8; 135.0; 141.1; 143.6; 146.8.

EXAMPLE 4

(1) Triphenylphosphine (262 g, 1.0 mol), vinylpseudoionol (252 g, 96%, 1.1 mol) and 800 ml butanol are mixed, and a solution of sulfamic acid (97 g, 1.0 mol) dissolved in 200 ml butanol at a temperature of 80~85° C. is added to it, allowed to react for 2 hr under heat preservation after finishing the addition, and the pH of the solution is neutral. The reaction mixture appears faint yellow. The reaction mixture is analyzed by HPLC to find that vinylpseudoionol is completely converted to phosphonic salt and its E/Z ratio is 2.9:1.

Next, 100 ml of deionized water is added into the reaction mixture, extracted with 500 ml of n-hexane for 3~5 times, and then the n-hexane layer recycled for reutilization, and the extracted unreacted triphenylphosphine may be crystallized for reutilization. The butanol in butanol solution containing phosphonic salt is recycled, and the solution is extracted with 2000 ml of dichloromethane to obtain 550 g of phosphonic salt after removing solvent, the yield of the phosphonic salt is 89.1%, and the content of the phosphonic salt analyzed by HPLC is 98%.

(2) Refinement: a dichloromethane solution of the phosphonic salt obtained from step (1) is washed with 500 ml of 10% sodium bromide aqueous solution each time for 3 times to obtain a dichloromethane layer after recycling most of the dichloromethane, and 1500 ml of ethyl acetate is added, and then 500 ml of a mixed solution containing dichloromethane and ethyl acetate is evaporated, and a residue is cooled and crystallized, and then obtain 81 g of phosphonic salt after filtrating and drying, its E/Z ratio is 0.3:11.0, and obtain 467.5 g of solid after removing solvent in mother liquor, its E/Z ratio is 94.5:1, and the yield of refinement is 85.0%, and the total yield of two steps (1) & (2) is 75.7%.

Determination of Product Structure:

$^1$HNMR (δ, ppm,400 MHz, MeOD): 1.45, 1.55, 1.65, 1.76(s, 12H, CH$_3$); 2.05~2.07,2.15~2.18(m, 4H, CH$_2$); 4.66~4.72(m, 2H, P—CH$_2$); 5.06~5.08, 5.30~5.33, 5.80~5.82, 6.00~6.03, 6.32~6.36 (m, 5H, C=CH, CH=CH); 7.72~7.88(m, 15H, ph).

$^{13}$CNMR (δ, ppm, 100 MHz, MeOD): 13.2; 17.5; 24.1; 25.6; 32.6; 40.4; 117.0; 137.6; 125.5; 127.6; 130.4; 132.6; 133.8; 135.0; 141.1; 143.6; 146.8.

EXAMPLE 5

(1) Triphenylphosphine (262 g, 1.0 mol), vinylpseudoionol (252 g, 96%, 1.1 mol) and 1000 ml pentanol are mixed, and a solution of methanesulfonic acid (96 g, 1.0 mol) dissolved in 200 ml pentanol at a temperature of 95~100° C. is added to it, allowed to react for 2 hr under heat preservation after finishing the addition, and the pH of the solution is neutral. The reaction mixture appears faint yellow. The reaction mixture is analyzed by HPLC to find that vinylpseudoionol is completely converted to phosphonic salt and its E/Z ratio is 3.5:1. Next, 100 ml deionized water is added into the reaction mixture, extracted with 500 ml of n-hexane for 3~5 times, and the n-hexane layer recycled for reutilization, and the extracted unreacted triphenylphosphine may be crystallized for reutilization. The pentanol in pentanol solution containing phosphonic salt is recycled, and the solution is extracted by 2000 ml dichloromethane to obtain 521 g phosphonic salt after removing solvent, the yield of the phosphonic salt is 84.3%, and the content of the phosphonic salt analyzed by HPLC is 96.5%.

(2) Refinement: a dichloromethane solution of the phosphonic salt obtained from step (1) is washed with 500 ml of a 5% sodium bromide aqueous solution each time for 3 times to obtain a dichloromethane layer after recycling most of the dichloromethane, and then 1500 ml of ethyl acetate is added, and then 500 ml of a mixed solution containing dichloromethane and ethyl acetate is evaporated, and a residue is cooled and crystallized, and then obtain 70 g of phosphonic salt after filtrating and drying, its E/Z ratio is 1:11.5, and then obtain 438 g of solid after removing solvent in mother liquor, its E/Z ratio is 98.5:1, and the yield of refinement is 84.1%, and the total yield of two steps (1) and (2) is 70.1%.

Determination of Product Structure:

$^1$HNMR (δ, ppm,400 MHz, MeOD): 1.45, 1.55, 1.65, 1.76(s, 12H, CH$_3$); 2.05~2.07,2.15~2.18(m, 4H, CH$_2$); 4.66~4.72(m, 2H, P—CH$_2$); 5.06~5.08, 5.30~5.33, 5.80~5.82, 6.00~6.03, 6.32~6.36 (m, 5H, C=CH, CH=CH); 7.72~7.88(m, 15H, ph).

$^{13}$CNMR (δ, ppm, 100 MHz, MeOD): 13.2; 17.5; 24.1; 25.6; 32.6; 40.4; 117.0; 137.6; 125.5; 127.6; 130.4; 132.6; 133.8; 135.0; 141.1; 143.6; 146.8.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. A method for preparing a phosphonic salt of Formula I, comprising reacting 3, 7, 11-trimethyldodec-1, 4, 6, 10-tetraene-3-ol of Formula II with triarylphosphine and an acid in an alcohol solvent at a temperature of 50-100° C. to produce a phosphonic salt of Formula I, wherein the acid is added to a reaction system of the 3, 7, 11-trimethyldodec-1, 4, 6, 10-tetraene-3-ol of Formula II and triarylphosphine in the alcohol solvent,

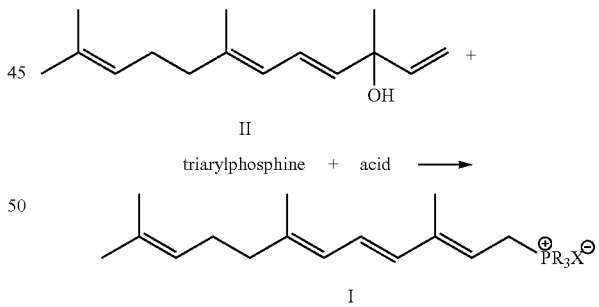

wherein the acid is sulfamic acid or methanesulphonic acid, the alcohol solvent is a straight-chain monohydric alcohol containing C1-C5, R is phenyl, and X is an anion of sulfamic acid or methanesulphonic acid.

2. The method according to claim 1, wherein the straight-chain monohydric alcohol is methanol or ethanol.

3. The method according to claim 1, wherein 3,7,11-trimethyldodec-1,4,6,10-tetraene-3-ol of Formula II is obtained by reacting pseudoionone with a Grignard reagent of chloroethylene.

4. The method according to claim 1, wherein the acid is dropped into the reaction system.

5. The method according to claim 1, wherein the reaction temperature is 60-65° C.

6. The method according to claim 1, wherein a E/Z ratio of the phosphonic salt of Formula I is 2.5:1.

7. The method according to claim 1, further comprising adding 100 ml deionized water into the phosphonic salt of Formula I, and then extracting with 500 ml n-hexane for 3-5 times, recycling n-hexane for reutilization, and extracting a methanol solution containing phosphonic salt of Formula I with 2000 ml dichloromethane to obtain a dichloromethane solution containing phosphonic salt of Formula I, and then obtaining phosphonic salt of Formula I after removing solvent.

8. The method according to claim 7, further comprising washing the dichloromethane solution containing phosphonic salt of Formula I with 500 ml of 5% sodium bromide aqueous solution each time for 3 times, and adding 1500 ml ethyl acetate into a dichloromethane layer after removing dichloromethane, and evaporating 500 ml of a mixed solution containing dichloromethane and ethyl acetate, and cooling the residue to produce crystals, and then filtrating and drying to produce a phosphonic salt of Formula I with E/Z ratio of 1:11.5, and obtaining phosphonic salt of Formula I with E/Z ratio of 94.5:1 after removing solvent of a mother liquor.

9. The method according to claim 1, wherein the acid is added to the reaction system to maintain a neutral pH of the reaction system.

10. The method according to claim 4, wherein the acid is dropped into the reaction system to maintain a neutral pH of the reaction system.

11. The method according to claim 1, wherein the reaction system consists of 3, 7, 11-trimethyldodec-1, 4, 6, 10-tetraene-3-ol of Formula II and triarylphosphine in the alcohol solvent and the acid added to the reaction system is in an alcohol solvent.

12. The method according to claim 1, wherein the 3, 7, 11-trimethyldodec-1, 4, 6, 10-tetraene-3-ol of Formula II is added to the triarylphosphine in a first portion of the alcohol solvent, the acid is added to a second portion of the alcohol solvent, and the acid in the second portion of the alcohol solvent is added to the 3, 7, 11-trimethyldodec-1, 4, 6, 10-tetraene-3-ol of Formula II and triarylphosphine in the first portion of the alcohol solvent.

13. The method according to claim 12, wherein the acid in the second portion of the alcohol solvent is added to the 3, 7, 11-trimethyldodec-1, 4, 6, 10-tetraene-3-ol of Formula II and triarylphosphine in the first portion of the alcohol solvent to maintain a neutral pH.

14. The method according to claim 1, wherein the triarylphosphine is triphenylphospine.

* * * * *